United States Patent [19]

Rombouts et al.

[11] Patent Number: 4,672,034

[45] Date of Patent: Jun. 9, 1987

[54] OXIDATIVE ENZYME-CATALYZED CROSSLINKING OF BEET PECTINS

[75] Inventors: Franciscus M. Rombouts, Heteren, Netherlands; Jean-Francois Thibault, Orvault; Christiane Mercier, Nantes, both of France

[73] Assignee: Institut National de la Recherche Agronomique, Nantes, France

[21] Appl. No.: 603,318

[22] Filed: Apr. 24, 1984

[30] Foreign Application Priority Data

Apr. 29, 1983 [FR] France ................................ 83 07208

[51] Int. Cl.$^4$ ...................... C12P 19/04; C08B 30/04; C08B 37/06; A23L 1/04
[52] U.S. Cl. ...................................... 435/101; 127/33; 127/67; 424/115; 424/195.1; 426/48; 426/52; 426/577; 435/275; 536/2
[58] Field of Search ...................... 426/48, 577, 49, 50, 426/52; 127/32, 33, 36, 67, 29; 536/2; 435/274, 275, 101; 424/115, 195.1

[56] References Cited

FOREIGN PATENT DOCUMENTS

| | | |
|---|---|---|
| 244249 | 3/1947 | Fed. Rep. of Germany . |
| 237377 | 3/1947 | Switzerland . |
| 0429795 | 11/1974 | U.S.S.R. ............................. 426/577 |

OTHER PUBLICATIONS

Chemical Abstracts, vol. 83, No. 15, Oct. 13, 1975, p. 217, No. 128149m, I. L. Gatfield et al., "Enzymic Reactions in the . . . ".
Chemical Abstracts, vol. 81, 1974, p. 122, No. 87153w, P. J. Brignac, Jr., et al., "Oxidation of 2-Naphthol, 1-Naphthol, . . . ".
"Cereal Foods World"; vol. 23, No. 7, Jul. 1978, pp. 374-336; Oxidative Gelation of Wheat Flour Pentosans: A New Way of Cross-Linking Polymers".
Chemical Abstracts: vol. 96: 102713j, Vamos-Vigyazo, et al., Chem, Mikrobiol, Technol. Lebensm, 1981, 7(3), 77-86.
Whistler, R. L., Industrial Gums 2nd ed., Academic Press, NY and London, 1973, pp. 436-445, 450, 451.

*Primary Examiner*—David M. Naff
*Attorney, Agent, or Firm*—Burns, Doane, Swecker & Mathis

[57] ABSTRACT

Beet pectin is crosslinked with an oxidizing system containing an oxidizing agent and an enzyme such as peroxidase that uses the oxidizing agent as a substrate. The crosslinked beet pectin is useful as a thickener or gelling agent in food, cosmetic and pharmaceutical products.

23 Claims, No Drawings

OXIDATIVE ENZYME-CATALYZED CROSSLINKING OF BEET PECTINS

1. FIELD OF THE INVENTION

The invention relates to a process for modifying beet pectins, to the products obtained by this process, and to their applications, especially in the foodstuff, cosmetic or pharmaceutical industries.

2. DESCRIPTION OF THE PRIOR ART

The pectins are natural molecules consisting of partially methylated polygalacturonic acid, that is to say pectins in which the acid groups are partially esterified with methanol; the base unit of these polymers corresponds to the formula:

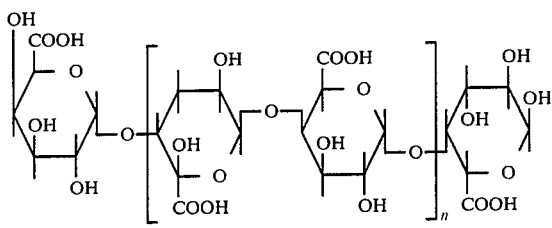

Certain of these pectins are used to form aqueous gels or to thicken various media. The ability to form these gels, and the conditions under which they are formed, essentially depend on the structure of the pectin, which itself depends on the plant from which it has been extracted and on the process of extraction. Thus, at the present time only pectins extracted from apples and citrus fruits are used to prepare either jellies and jams, or cosmetics, or thickening and dehydrating adjuvants for various compositions.

It is known that the so-called highly methoxylated pectins, that is to say those in which at least 50% of the carboxylic groups of the galacturonic acids are esterified with methanol, gel in the presence of sucrose and in an acid medium; thus they are particularly used in producing jellies and jams.

The less highly methoxylated pectins gel in the presence of $Ca^{2+}$ ions, due to the formation of coordination bonds between the oxygen atoms and the cation; however, the preparation of suitable gels is a delicate matter because of secondary precipitation phenomena, especially when the $Ca^{2+}$ is added to the pectins.

Certain natural pectins, probably because they carry substituents on the polygalacturonic acid chain, do not form gels when they are subjected to the known gelling processes, namely either addition of sucrose in an acid medium or addition of $Ca^{2+}$.

This information on the gelling of pectins is to be found in particular in the work "Les polymères végétaux, polymères pariétaux et alimentaires non azotés" ("Plant Polymers, Parietal and Edible Nitrogen-Free Polymers"), Bernard MONTIES and Claude COSTES—Editions Gauthier-Villars (1980) pages 232–251.

It is known that the pectins extracted from beet pulps do not form suitable gels by the processes referred to above; it is believed that the presence of acetyl groups resulting from the esterification of certain hydroxyl groups plays a part in this absence of gelling; as these polymers have relatively low molecular weights they can moreover not be used as thickeners. It is for this reason that no industrial use is currently known, in spite of the abundance of this raw material: pectin constitutes 15 to 20% of the solids content of beet residues as likewise 15 to 20% of the solids content of apple residues.

Thus, the process according to the invention, which enables the use of these pectins after they have been modified, is of great economic value because it permits commercial use of the residues from beet, especially from sugar-beet.

DESCRIPTION OF THE INVENTION

The invention relates to a process for the treatment of beet pectins which consists of carrying out an enzyme-catalyzed oxidative crosslinking of the pectins, leading to products having higher molecular weights, which are soluble in water or give gels with water. The crosslinking involves the reaction with an oxidizing system comprising an oxidizing agent, especially hydrogen peroxide, and an enzyme of which the oxidizing agent is a substrate, for example a peroxidase in the case of $H_2O_2$. The invention also relates to the modified pectins obtained by this crosslinking process, the aqueous gels resulting from certain embodiments as well as the methods of use of these modified pectins and these gels as thickeners and gelling agents, especially in the food, cosmetic or pharmaceutical industries.

The process of the invention has never before been used for treating pectins; it has moreover been found that it can only be applied successfully to certain pectins. Pectins from apple, citrus fruit, cherry, apricot or potato residues do not crosslink under these conditions; however, the process gives good results with pectins derived from beets, especially from sugar-beets, regardless of their origin.

The pectins are extracted from the beet pulps and residues in accordance with processes known per se, for example by treatment of the pulps with a hot acid aqueous solution for several hours; thus, the recovered pulps can be brought into contact for 1 to 2 hours with a dilute solution of sulphuric acid having a pH from 1.5 to 2 at a temperature of 80° C. about. Where such an extraction process results in pectin solutions of suitable concentration, the crosslinking can be carried out directly in said solution after having brought the latter to a suitable pH; alternatively, the pectins are precipitated from their extraction medium in accordance with methods known per se, then isolated by filtration and dried to give powders which are subsequently treated by the process according to the present invention.

According to the invention as generally contemplated, the oxidative enzyme-catalyzed crosslinking is carried out by adding to an aqueous pectin solution an amount of peroxidase of from 0.01 mg to 1 mg per 1 g of pectin in the solution, and furthermore adding an aqueous hydrogen peroxide solution containing from 10 micromoles to 1 millimole of $H_2O_2$ per 1 g of pectin. If necessary any remaining peroxide from the crosslinking reaction process is decomposed by adding an enzyme, for example, such as catalase.

According to a preferred embodiment of the invention, the oxidative enzyme-catalyzed crosslinking is carried out by adding to the aqueous beet pectin solution of a given concentration from 0.3 to 0.6 mg of peroxidase per gram of pectin and approximately from 13 μmoles to 36 μmoles of hydrogen peroxide, in aqueous solution, per gram of pectin. Crosslinking is also carried out by adding from 0.03 mg to 0.1 mg of peroxidase and 0.25 to 1.0 millimole of hydrogen peroxide per gram of pectin in the solution; in this case, the remaining peroxide is decomposed by adding another enzyme, namely catalase. In a preferred embodiment, the concentration added is about 0.1 mg of catalase for each millimole of $H_2O_2$. The molecular weight of the modified pectins thus obtained depends on the concentrations and relative proportions of the reactants.

Since dilute solutions of hydrogen peroxide are of low stability, the reactant is preferably prepared at the time of use from commercial 30% (by weight) $H_2O_2$ solutions; the dilutions used are, for example, from 0.01 to 1% of $H_2O_2$ in $H_2O$ (volume/volume).

The peroxidase can be of animal or vegetable origin; advantageously, type I horseradish peroxidase, sold by SIGMA (U.S.A.), is used; it can either be dissolved in the aqueous solution or coupled to an insoluble carrier which will be brought into contact with the reaction medium, in a manner known per se for enzymatic reactions.

The pH of the aqueous pectin solutions can be between about 4 and 7; it is of course so selected that the enzyme of the oxidizing system can promote the oxidation and that the pectins are not degraded.

Depending on the concentration of the aqueous beet pectin solution, on the nature of the pectin and on the amount of oxidizing system, there is formed at ambient temperature, within a few minutes after addition of the oxidizing system, either a gel or a solution of higher viscosity than that of the starting solution, containing the crosslinked pectin.

According to another embodiment of the invention, the suitable concentration of the starting pectin solution to give either a solution of increased viscosity or gelation is determined prior to carrying out the crosslinking. It has been found that in general, for beet pectins having a viscosimetric molecular weight of 40,000 to 50,000, an acetylation rate of 30 to 35% and a content in neutral sugar groups of between 15 and 20%, aqueous solutions whose pectin content is less than 1.5 g/100 ml cannot be gelled while, on the other hand, aqueous solutions of concentration higher than 2 g/100 ml result in thick gels, when small amounts of oxidizing system are reacted; with an excess of $H_2O_2$ and of enzyme, gels are obtained with pectin concentrations as low as 0.3 g/100 ml. In general, the beet pectin solutions have a maximum concentration of 4 g/100 ml, given the limited solubility of pectins in water.

The novel modified pectins according to the present invention can be recovered from the aqueous media in which they have been produced; for example they are precipitated out by adding a solvent, such as alcohol or a keytone such as acetone, to the aqueous media, or by adding a neutral non-organic salt such as mineral salts (salting-out); thereafter, the solids are recovered by filtration or centrifugation and dried at ambient pressure or under vacuum with moderate heating, at about 40° C. In general, at least one volume, preferably about 4 volumes, of precipitation solvent is added per volume of the aqueous solution.

The possibility of isolating the gelation pectins in the state of a dry powder is another advantage of the invention; the previously known gels from apple pectins or citrus fruit pectins did not possess this property. The powder produced from the gels according to the invention, when brought into contact of the appropriate amount of water, again gives a gel.

The modified pectin powders obtained according to the process of the invention can be used as thickening or gelling agents; they are very hydrophilic and are capable of taking up large amounts of water.

In particular, these modified pectins can be used to prepare foodstuff products, such as milk-based desserts, for example custards which can be prepared at ambient temperature. They can also be used advantageously in the composition of ice desserts; it has been demonstrated that the gels according to the invention are perfectly stable when subjected successively to freezing and thawing conditions, between −20° C. and ambient temperature.

Another advantageous use of the pectins according to this invention is the preparation of ointments which are used in the cosmetic or pharmaceutical industries in which the pectine are carriers.

According to another embodiment of the invention, the aqueous solution containing the beet pectins is gelled in the presence of various effective ingredients which results in the formation of particularly homogeneous or stabilized compositions. Such a process is used, for example, for microencapsulation of flavourings, of compounds having pharmacological effectiveness, etc., or for the detoxification of certain media by, for example, trapping heavy metals present in them.

Illustrative embodiments of the invention are given below.

EXAMPLE 1

Preparation of a solution of modified pectins:

1 ml of an aqueous hydrogen peroxide solution is added to 10 ml of an aqueous beet pectin solution of pH 6 and containing 0.3 mg of horseradish peroxidase per gram of pectin, so as to give 13 $\mu$moles of $H_2O_2$ per gram of pectin. Crosslinking is ended after a few minutes' stirring at ambient temperature.

This process was applied to solutions having various pectin concentrations, and the viscosity of the solutions obtained was measured. Table I shows the experimental results expressed in intrinsic viscosities and in molecular weights, calculated in accordance with the method described by H. S. OWENS, H. LOTZKAR, T. H. SCHULTZ and W. D. MACLAY in J. Am. Chem. Soc. 68, 1 628-1 632 (1946).

TABLE 1

| Pectin concentration (g/100 ml) | Intrinsic viscosity ($cm^3/g$) | Molecular weight |
| --- | --- | --- |
| Standard* | 248 | 46,000 |
| 0.6 | 435 | 70,000 |
| 0.9 | 468 | 73,900 |
| 1.5 | 461 | 73,000 |

*Aqueous pectin solution without addition of the cross-linking oxidising system.

EXAMPLE 2

Gelling of an aqueous beet pectin solution:

0.1 ml of an aqueous peroxidase solution (of concentration 0.1 mg/ml) and 0.1 ml of an aqueous hydrogen peroxide solution of concentration 4.3 $\mu$moles/ml are added to 1 ml of a beet pectin solution (of concentration 3 g/100 ml) at about pH 6; the mixture is stirred mechanically for 1 to 2 minutes until it gels. The gel is translucent and remains stable for several months at ambient temperature.

Table II shows the rheological properties of a gel prepared according to this process and those of an amide pectin gel, prepared according to the method described by S. A. BLACK and C. J. B. SMIT in J. Food Science 37 726-29 (1972) by way of comparison.

TABLE II

| Gel | "Apparent" modulus of rigidity (g/cm) | Breaking load (g) | Deformation (cm) |
|---|---|---|---|
| Amidepectin | 15.2 | 11.80 | 0.45 |
| Example 2 | 11.6 | 36.3 | 0.67 |

The measurements were carried out with an IN-STRON ® apparatus.

These results show that the gel according to the invention is less "brittle" than the gel prepared according to a known method.

EXAMPLE 3

Preparation of a modified pectin powder:

A beet pectin gel is prepared as described in Example 2. 4 volumes of aqueous ethanol (of 96% V/V are added, with stirring; the modified pectins which precipitate, are recovered by filtration and then dried at ambient temperature.

The hydrophilic strength of this powder was determined by bringing the powder into contact with excess water in a graduated vessel and measuring the volume of gel formed at equilibrium:

110 ml of a gel were obtained with 1 g of beet pectin powder prepared as described above.

EXAMPLE 4

Using the same method of working as that described in Example 2 and varying the relative proportions of the reactants, the results in Table III are obtained.

TABLE III

| Pectin concentration (g/l) | Peroxidase concentration (mg/l) | $H_2O_2$ concentration (mmole/l) | Gelation | increase in molecular weight |
|---|---|---|---|---|
| 6.26 | 0.25 | 2 | + | |
| 5.01 | 0.25 | 2 | + | |
| 3.76 | 0.25 | 2 | − | |
| 2.51 | 0.25 | 2 | − | |
| 5.45 | 0.67 | 2 | − | |
| 5.61 | 0.1 | 2 | − | 140% |
| 3.48 | 1.7 | 8.3 | + | |
| 3.5 | 2.0 | 2 | + | |
| 3.01 | 8.3 | 4 | − | 150% |
| 4.88 | 0.07 | 0.7 | − | 210% |
| 3.19 | 0.04 | 1.3 | − | 180% |

We claim:

1. A process for modifying beet pectins comprising reacting a beet pectin starting solution in a reaction medium with an oxidizing system, said oxidizing system comprising at least one oxidizing agent and a peroxidase which has said oxidizing agent as a substrate wherein the oxidizing system is employed in an amount effective and for a time sufficient to crosslink the pectin to form a modified beet pectin solution of increased viscosity or a gel.

2. A process as claimed in claim 1, wherein the oxidizing agent is hydrogen peroxide.

3. A process as claimed in claim 2, wherein said starting solution is an aqueous pectin solution, and said process is carried out by (1) adding to the aqueous pectin solution an amount of peroxidase of from 0.01 mg to 1 mg per 1 g of pectin; and (2) thereafter adding an aqueous hydrogen peroxide solution containing from 10 $\mu$moles to 1 mmole of $H_2O_2$ per 1 g of pectin.

4. A process as claimed in claim 3, wherein after crosslinking, the modified pectin is precipitated by adding to the reaction medium an agent selected from the group consisting of a solvent and a salting-out agent, and recovering and drying the precipitate to form a powder.

5. A process as claimed in claim 3, wherein about 0.1 mg of catalase per about 1 mmole of $H_2O_2$ is added to decompose unreacted $H_2O_2$.

6. A process according to claim 1 wherein a modified beet pectin solution of increased viscosity is formed.

7. A process according to claim 2 wherein a modified beet pectin solution of increased viscosity is formed.

8. A process according to claim 3, wherein the pectin starting solution has a pectin concentration of less than 1.5 g/100 ml and the oxidizing system comprises from 0.3 to 0.6 mg of peroxidase and from 13 to 36 $\mu$moles of $H_2O_2$ per 1 g of pectin.

9. A process according to claim 4, wherein the pectin starting solution has a pectin concentration of less than 1.5 g/100 ml and the oxidizing system comprises from 0.3 to 0.6 mg of peroxidase and from 13 to 36 $\mu$moles of $H_2O_2$ per 1 g of pectin.

10. A process according to claim 1, wherein a gel is formed.

11. A process according to claim 2, wherein the pectin starting solution has a pectin concentration of greater than 2 g/100 ml and the oxidizing system comprises from 0.3 to 0.6 mg of peroxidase and from 13 to 36 $\mu$moles of $H_2O_2$ per 1 g of pectin.

12. A process according to claim 2 wherein the pectin starting solution has a pectin concentration of greater than 0.3 g/100 ml and the oxidizing system comprises from 0.03 to 0.1 mg of peroxidase and from 0.25 to 0.1 mmole of $H_2O_2$ per 1 g of pectin.

13. A process according to claim 4 wherein the powder is mixed with water to form an aqueous gel.

14. A water-soluble modified beet pectin prepared by the process as claimed in claim 6.

15. A water-soluble modified beet pectin prepared by the process as claimed in claim 7.

16. A water-soluble modified pectin prepared by the process as claimed in claim 8.

17. A modified pectin powder prepared by the process as claimed in claim 9.

18. A modified beet pectin capable of causing gelation of an aqueous medium produced by the process as claimed in claim 10.

19. A modified beet pectin capable of causing gelation of an aqueous medium, produced by the process as claimed in claim 11.

20. A modified beet pectin capable of causing gelation of aqueous medium produced by the process as claimed in claim 12.

21. An aqueous gel produced by the process of claim 13.

22. A process for thickening comprising the steps of reacting a beet pectin starting solution in a reaction medium with an oxidizing system, said oxidizing system comprising at least one oxidizing agent and a peroxidase which has the said oxidizing agent as a substrate wherein the oxidizing system is employed in an amount effective and for a time sufficient to crosslink the pectin to form an ungelled water-soluble modified beet pectin solution of increased viscosity, and adding the water-soluble modified beet pectin as a thickening agent to foodstuff products, cosmetics products or pharmaceutical products.

23. A process for gelling comprising the steps of reacting a beet pectin starting solution in a reaction medium with an oxidizing system, said oxidizing system comprising at least one oxidizing agent and a peroxidase which has the said oxidizing agent as a substrate wherein the oxidizing system is employed in an amount effective and for a time sufficient to crosslink the pectin to form a modified beet pectin and gel the reaction medium, and adding the modified beet pectin as a gelling agent to foodstuff products, cosmetics products or pharmaceutical products.

* * * * *